United States Patent [19]

Delecluse et al.

[11] Patent Number: 5,304,484
[45] Date of Patent: Apr. 19, 1994

[54] NON-HEMOLYTIC MOSQUITOCIDAL MICROORGANISMS

[75] Inventors: Armelle Delecluse, Thiers Sur Theve; Andre Klier, Neuilly S/Marne; Georges Rapoport, Paris, all of France

[73] Assignee: Institut Pasteur, Paris, France

[21] Appl. No.: 760,075

[22] Filed: Sep. 13, 1991

[51] Int. Cl.$^5$ .................. C12N 15/32; C12N 15/75; C12N 1/21

[52] U.S. Cl. .................. 435/252.31; 435/69.1; 435/71.2; 435/172.1; 435/172.3; 435/252.3; 435/252.5; 435/320.1; 435/832; 536/23.71; 935/10; 935/29; 935/56; 935/74; 514/2

[58] Field of Search ............... 435/69.1, 71.2, 172.1, 435/172.3, 252.3, 252.31, 252.5, 320.1, 832; 514/2; 536/27, 23.71; 935/10, 29, 56, 74

[56] References Cited

PUBLICATIONS

James D. Watson "Molecular Biology of the Gene" The Benjamin/Cummings Publishing Co. Menlo Park, CA. p. 313 (1987).
Bourgouin, C. et al. "Characterization of the Genes Encoding the Hemolytictoxin . . ." Mol. Gen. Genet. 205:390–397 (1986).
Delécluse, A. et al. "Deletion by In vivo Recombination . . ." J. of Bacteriology 173:3374–3381 (Jun. 1991).
A. M. Albertini et al., "Amplification Of A Chromosomal Region In Bacillus Subtilis", J. Bacteriol., 162:1203–1211 (1985).
J. L. Armstrong et al., "Delta Endotoxin Of Bacillus Thuringiensis Subsp. Israelensis", J. Bacteriol., 161:39–46 (1985).
C. Bourgouin et al., "A Bacillus Thuringiesis Subsp. Israelensis Gene Encoding A 125-Kilodalton Larvicidal Polypeptide Is Associated With Inverted Repeat Sequences", J. Bacteriol., 170:3575–3583 (1988).
P. Y. K. Cheung et al., "Separation Of Three Biologically Distinct Activities From The Parasporal Crystal Of Bacillus Thuringiensis Var. Israelensis", Curr. Microbiol., 12:121–126 (1985).
C. N. Chilcott et al., "Comparative Toxicity Of Bacillus Thuringiensis Var. Israelensis Crystal Proteins In Vivo And In Vitro", J. Gen. Microbiol., 134:2551–2558 (1985).
E. W. Davidson et al., "Isolation And Assay Of The Toxic Component From The Crystals Of Bacillus Thuringiensis Var. Israelensis", Curr. Microbiol., 11:171–174 (1984).
A. Delecluse, "Caracterisation Des Genes Codant Por Les Toxines De Bacillu Thuringiensis Serovar Israelensis Actif Sur Les Larves De Dipteres, Vecteurs De Maladies Tropicales" These de Doctorate De L'Universite Paris VII (Jan. 15, 1991).
A. Delecluse et al., "Specificity Of Action On Mosquito Larvae Of Bacillus Thuringiensis Israelensis Toxins Encoded By Two Different Genes", Mol. Gen Genet, 214:42–47 (1988).
B. A. Federici et al., "Parasporal Body Of Bacillus Thuringiensis Israelensis. Structure, Protein Composition, And Toxicity", pp. 16–44. In H. de Barjac, and D. J. Sutherland (ed.), Bacterial Control of Mosquitoes and Black Flies; Biochemistry, Genetics and Applications of Bacillus thuringiensis israelensis and Bacillus sphaericus. Rutgers University Press, New Brunswick (1990).

(List continued on next page.)

*Primary Examiner*—Robert A. Wax
*Assistant Examiner*—Rebecca Prouty
*Attorney, Agent, or Firm*—Finnegan, Henderson, Farabow, Garrett & Dunner

[57] ABSTRACT

The cyta gene encoding the 28 kDa polypeptide of *Bacillus thuringiensis israelensis* crystals was disrupted in the 72 MDa resident plasmid by in vivo recombination. The absence of the 28 kDa protein in *B. thuringiensis israelensis* did not affect the crystallization of the other toxic components of the parasporal body. However, the absence of the 28 kDa protein did abolish the hemolytic activity of *B. thuringiensis* serovar *israelensis* crystals. The mosquitocidal activity of the 28 kDa protein-free crystals did not differ significantly from the wild-type crystals.

7 Claims, 5 Drawing Sheets

PUBLICATIONS

L. H. Goldberg et al., "A Bacterial Spore Demonstrating Rapid Larvicidal Activity Against Anopheles Sergentii, Uranotaenia Unguiculata, Culex Univitatus, Aedes Aegypti And Culex Pipiens", Mosq. News, 37:355-358 (1977).

J. M. Gonzalez, Jr. et al., "A Large Transmissible Plasmid Is Required For Crystal Toxin Production In Bacillus Thuringiensis Variety Israelensis", Plasmid, 11:28-38 (1984).

G. A. Held et al., "Effect Of Removal Of The Cytolytic Factor Of Bacillus Thuringiensis Subsp. Israelensis On Mosquito Toxicity", Biochem. Biophys. Res. Commun., 141:937-941 (1986).

H. Hofte et al., "Insecticidal Crystal Proteins Of Bacillus Thuringiensis", Microbiol. Rev., 53:242-255 (1989).

J. M. Hurley et al., "Separation Of The Cytolytic And Mosquitocidal Proteins Of Bacillus Thuringiensis Subsp. Israelensis", Biochem. Biophys. Res. Commun., 126:961-965 (1985).

J. E. Ibarra et al., "Isolation Of A Relatively Nontoxic 65-Kilodalton Protein Inclusion From The Parasporal Body Of Bacillus Thuringiensis Subs. Israelensis", J. Bacteriol., 165:527-533 (1986).

J. P. Insell et al., "Composition And Toxicity Of The Inclusion Of Bacillus Thuringiensis Subsp. Israelensis", Appl. Environ. Microbiol., 50:56-62 (1985).

L. Janniere et al., "Stable Gene Amplification In The Chromosome Of Bacillus Subtilis", Gene, 40:47-55 (1985).

K. M. McLean et al., "Expression In Escherichia Coli Of A Cloned Crystal Protein Gene Of Bacillus Thuringiensis Subsp. Israelensis", J. Bacteriol., 169:1017-1023 (1987).

J. T. Nishiura, "Fractionation Of Two Mosquitocidal Activities From Alkali-Solubilized Extracts Of Bacillus Thuringiensis Subspecies Israelensis Spores And Parasporal Inclusions", J. Invertebr. Pathol., 51:15-22 (1988).

M. A. Pfannenstiel et al., "Immunological Relationships Among Proteins Making Up The Bacillus Thuringiensis Subsp. Israelensis Crtystalline Toxin", Appl. Environ. Microbiol., 52:644-649 (1986).

K. Sen et al. "Cloning And Nucleotide Sequences Of The Two 130 kDA Insecticidal Protein Genes Of Bacillus Thuringiensis Var. Israelensis", Agric. Biol. Chem., 52:873-878 (1988).

W. E. Thomas et al., "Bacillus Thuringiensis Var. Israelensis Crystal δ-Endotoxin: Effects On Insect And Mammalian Cells In Vitro And In Vivo", J. Cell Sci., 60:181-197 (1983).

A. Undeen et al., "The Effect Of Bacillus Thuringiensis ONR60A Strain (Goldberg) On Simulium Larvae In The Laboratory", Mosq. News, 38:524-527 (1978).

B. Visser et al., "The Mosquitocidal Activity Of Bacillus Thuringiensis Var. Israelensis Is Associated With Mr 230,000 And 130,000 Crystal Proteins", FEMS Microbiol. Lett., 30:211-214 (1986).

E. S. Ward et al., "Assignment Of The δ-Endotoxin Gene Of Bacillus Thuringiensis Var. Israelensis To A Specific Plasmid By Curing Analysis", FEBS Lett., 158:45-49 (1983).

E. S. Ward et al., "Bacillus Thuringiensis Var. Israelensis δ-Endotoxin. Nucleotide Sequence And Characterization Of The Transcripts In Bacillus Thuringiensis And Escherichia Coli", J. Mol. Biol., 191:1-11 (1986).

E. S. Ward et al., "Cloning And Expression Of Two Homologous Genes Of Bacillus Thuringiensis Subsp. Israelensis Which Encode 130-Kilodalton Mosquitocidal Proteins", J. Bacteriol., 170:727-735 (1988).

E. S. Ward et al., "Cloning And Expression In Escherichia Coli Of The Insecticidal δ-Endotoxin Gene Of Bacillus Thuringiensis Var. Israelensis", FEBS Lett., 175:377-382 (1984).

E. S. Ward et al., "Bacillus Thuringiensis Var. Israelensis δ-Endotoxin. Cloning And Expression Of The Toxin In Sporogenic And Asporogenic Strains Of Bacillus Subtilis", J. Mol. Biol., 191:13-22 (1986).

D. Wu et al., "Synergism In Mosquitocidal Activity Of 26 And 65 kDA Proteins From Bacillus Thuringiensis Subsp. Israelensis Crystal", FEBS Lett., 190:232-236 (1985).

M. Young, "Gene Amplification In Bacillus Subtilis", J. Gen. Microbiol., 130:1613-1621 (1984).

NON-HEMOLYTIC MOSQUITOCIDAL MICROORGANISMS

BACKGROUND OF THE INVENTION

This invention relates to microorganisms having mosquitocidal activity but lacking hemolytic activity. The invention further relates to recombinant DNA molecules encoding mosquitocidal polypeptides of the invention, to vectors containing the DNA molecules, and to microorganisms expressing the polypeptides.

*Bacillus thuringiensis* serovar *israelensis* produces crystalline inclusions during sporulation that are toxic to mosquito and blackfly larvae (15, 35). These inclusions are, when solubilized, cytolytic for various mammalian cells including erythrocytes (33). The crystals are composed of at least four polypeptides of 135 kDa, 125 kDa, 68 kDa, and 28 kDa. It has been shown by electron microscopic studies that these crystals are composite, and consist of three major inclusion types differentiated on the basis of electron opacity, size and shape. Purification and protein analysis of one of three types of component crystal revealed that it only contained the 68 kDa polypeptide (21). It was therefore suggested that the 28 kDa and 125-135 kDa polypeptides could be assembled separately in the two other inclusions (21).

The diversity of the polypeptides has complicated the identification of the protein(s) responsible for larvicidal activity. The major difficulty in identifying the toxic polypeptide(s) was the purification of the different polypeptides. One solution to this problem was the cloning of the different genes. It has previously been shown that the toxin genes of *B. thuringiensis israelensis* were located on a 72 MDa resident plasmid (16, 37). No copy of the toxin gene was found on the chromosomal DNA. Cloning experiments with the 72 MDa plasmid and analysis of the cloned products clearly indicated that the 135 kDa, 125 kDa, and 68 kDA were involved in the toxicity to mosquitoes, alone or in combination (reviewed in Federici et al. (13)).

There is still controversy concerning the activity of the 28 kDA protein. Although biochemical and cloning experiments revealed that this polypeptide is responsible for the in vitro cytolytic activity of the crystals (4, 7, 18, 20, 27, 40), its contribution to the mosquitocidal activity remains unclear. Earlier biochemical studies suggested that the 28 kDa polypeptide was not toxic to *Aedes aegypti* larvae (9, 18, 20, 30, 36). However, several groups found that the purified protein was toxic for this insect, although the $LC_{50}$ observed was much higher than that obtained for the native, composite crystals (4, 10, 11, 22, 29). The cloning of the 28 kDa protein gene, now referred to as the cyta gene (19), on multicopy plasmids either in *Escherichia coli* (7, 27, 38, 40) or in *Bacillus subtilis* (41) did not resolve this controversy. One of the issues in the debate is the level of activity at which a polypeptide should be considered to be active. Moreover, if the 28 kDa protein acts synergistically with the 68 kDa and/or the 130 kDa polypeptides as suggested by Wu and Chang (42), Ibarra and Federici (21) and Chilcott and Ellar (10), the study of the cloned 28 kDa product alone does not reflect the involvement of this protein in the overall toxicity of the crystals.

There exists a need in the art for polypeptides having mosquitocidal activity and for recombinant vectors encoding the polypeptides and capable of expressing the polypeptides. Ideally, the microorganisms exhibiting mosquitocidal activity should be non-hemolytic.

SUMMARY OF THE INVENTION

This invention relates to a novel approach to elucidating the role of the 28 kDa polypeptide in the toxicity of the parasporal body. The experimental approach involved the disruption of the cyta gene present on the 72 MDa resident plasmid by in vivo recombination in *B. thuringiensis israelensis*. The toxicity of crystals depleted of the 28 kDa protein was determined on three mosquito species and compared to that obtained with native crystals. The results obtained indicated that the 28 kDa polypeptide has only a minor effect on the mosquitocidal activity, and that effect is restricted to *Anopheles Stephensi*. The depleted crystals lacked hemolytic activity.

More particularly, this invention aids in fulfilling the needs in the art by providing a recombinant microorganism comprising DNA sequences that encode polypeptides that are toxic to mosquito larvae, but do not possess hemolytic activity. In a preferred embodiment of the invention, the microorganism has the same larvicidal activity as that of the wild-type strain of *Bacillus thuringiensis israelensis*.

In a further embodiment of the invention, a composition is provided consisting essentially of at least one polypeptide having larvicidal activity, wherein the composition does not possess hemolytic activity.

Further, this invention provides a larvicidal microorgansim.

BRIEF DESCRIPTION OF THE DRAWINGS

This invention will be described in more detail with reference to the drawings in which.

B:BamHI:E:EcoRV;H:HpaI;P:PstI;Pv:PvuII;-RI:EcoRI

Figure 2A:
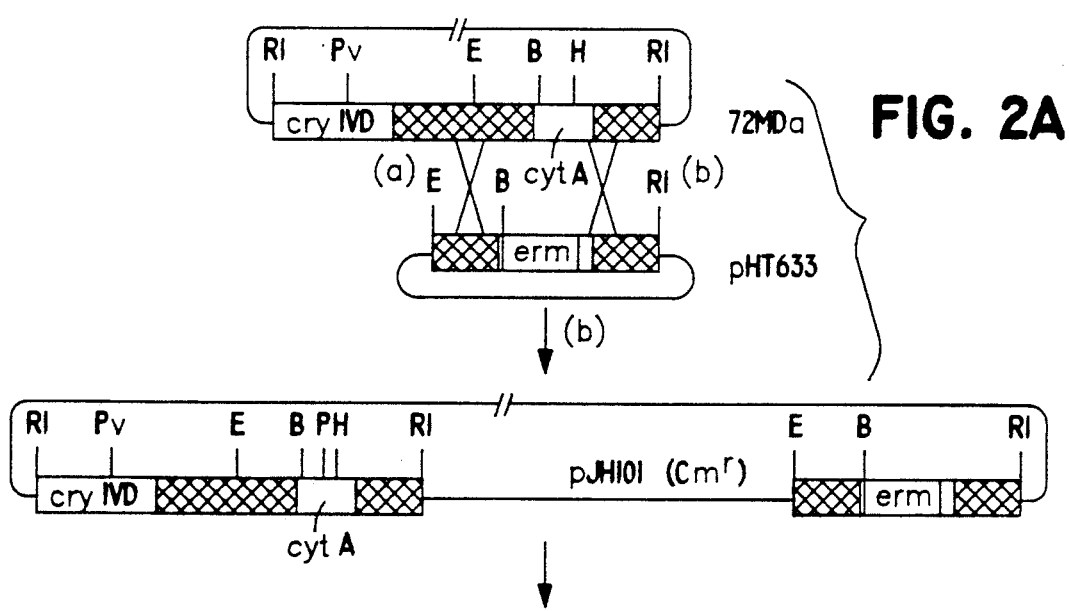
Figure 2B:
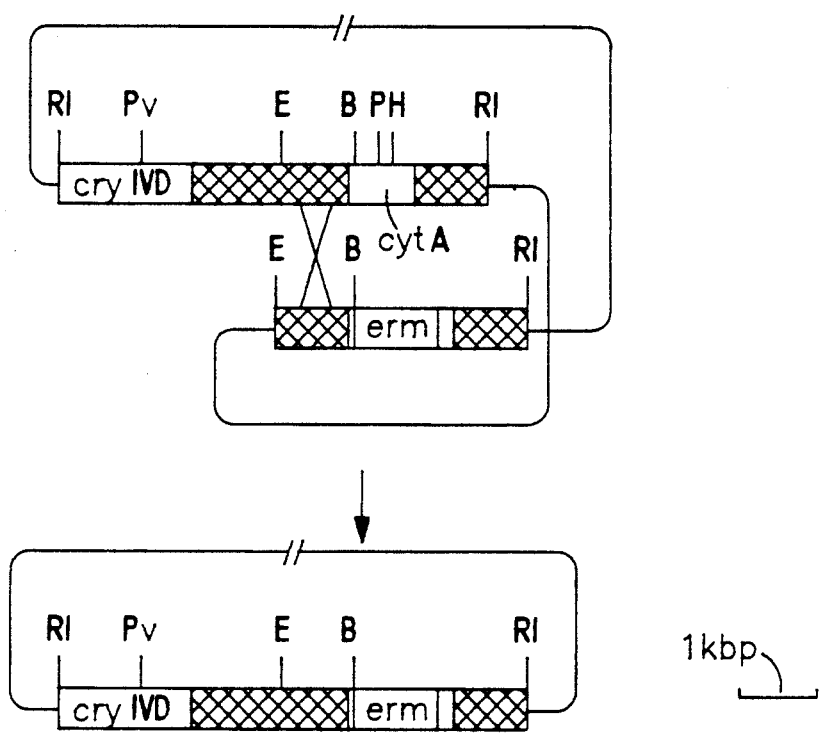

FIGS. 2A and 2B show construction of deleted cyta strains by homologous recombination in strain 4Q272. (A) depicts integration of the non-replicative plasmid pHT633 into the 72 MDa resident plasmid of *B. thuringiensis israelensis*. Plasmid pHT633 was used to transform the *B. thuringiensis israelensis* strain 4Q2-72. Transformants resulting from recombination between homologous regions were selected from Luria plates containing erythromycin (8 μg/ml). The crossover could occur either upstream (a) or downstream (b) from the erm gene. (B) depicts replacement of the cyta gene by an interrupted copy. Strain 4Q2-72 (::pHT633) was grown at 37° C. in Luria medium containing erythromycin (8 μg/ ml), but in absence of chloramphenicol allowing plasmid excision.

Figures 3A, 3B:
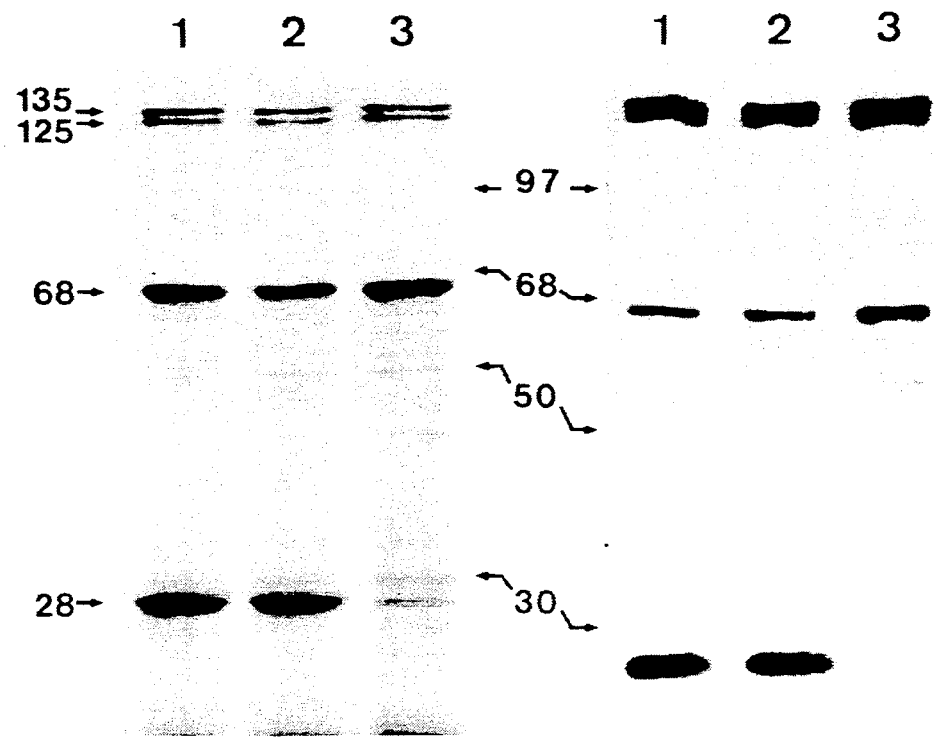

FIGS. 3A and 3B show the results of Southern blot analysis of DNA from wild-type and recombinant *B. thuringiensis israelansis* strains. Total DNA (10 μg) from each of strains 4Q2772, 4Q2-72 (::pHT633), and 4Q2-72 (cytA::exm) was hydrolyzed with EcoRI-EcoRV (A) or EcoRI (B), and subjected to electrophoresis on agarose gel. DNA fragments were transferred onto nitrocellulose and hybridized with the labeled plasmid pHT633. Lanes: 1,4Q2-72; 2, 4Q2-72 (::pHT633); 3, 4Q2-72 (cytA::erm); P, plasmid pHT633. Sizes of hybridizing DNA fragments (in kbp) are indicated in the margin.

Figures 4A, 4B:
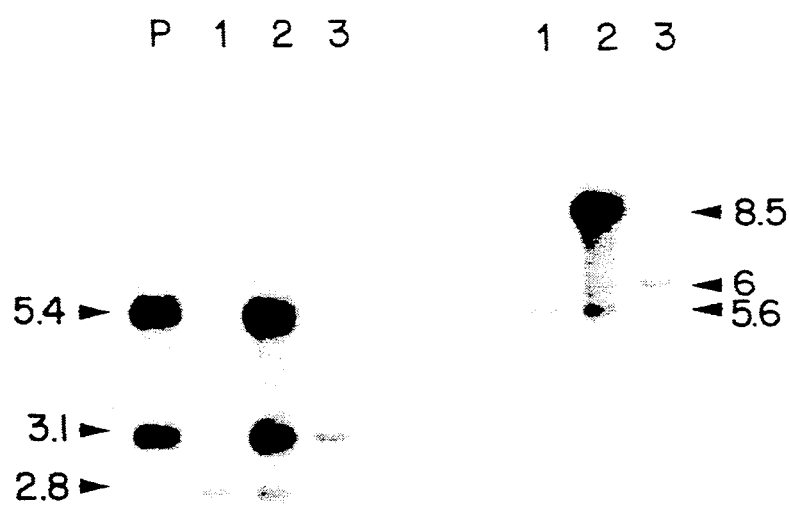

FIGS. 4A and 4B show the results of protein analysis of crystals from wild-type and recombinant *B. thuringiensis israelensis* strains. (A) depicts spore and crystal mixtures, corresponding to 10 μg of protein, which were subjected to electrophoresis on a 10% sodium dodecyl sulfatepolyacrylamide gel, followed by staining with Coomassie brilliant blue. (B) depicts spore and crystal mixtures corresponding to 1 μg of protein, which were subjected to electrophoresis (as above), and then transferred onto a nitrocellulose filter. The filter was incubated with antiserum (diluted 500 fold) raised against total solubilized crystals. Immunoreactive polypeptides were revealed with $^{125}$I labeled protein A. Lanes: 1,4Q2-72; 2,4Q2-72 (::pHT633); 3,4Q2-72 (cytA::-:erm). Numbers between parts A and B represent molecular weight (in kDa) of standard protein markers.

Figure 5A:
Figure 5B:

FIGS. 5A and 5B comprise electron micrographs of *B. thuringiensis israelensis* crystals. (A) corresponds to wild-type strain 4Q2-72. (B) corresponds to strain 4Q2-72 (cytA::e.rm). The numbers refer to the three major inclusion types according to Ibarra and Federici (21). The envelope that surrounds the parasporal body (PB) is indicated by arrows. S: Spore. All micrographs are at the same magnification with the bar representing 0.2 μm.

Figure 6:
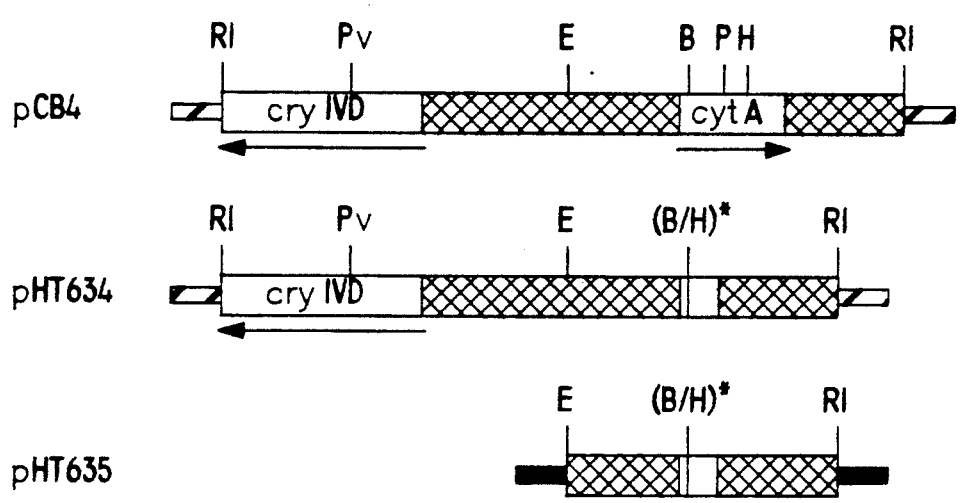

FIG. 6 illustrates the construction of recombinant plasmed pHT635. Plasmid pHT634 was constructed by deleting the 0.55 kbp BamHI-HpaI internal fragment of the cyta gene from plasmid pCB4. The BamHI site was made blunt by using the Klenow fragment of DNA polymerase I. Plasmid pHT635 was obtained by subcloning the 2 kb EcoRV - EcoRI from pHT634 into the vector pJH101. Both abbreviations for restriction sites and symbols used are those described for FIG. 1.

DETAILED DESCRIPTION OF THE INVENTION

Previous work has led to the identification of three mosquitocidal proteins in *B. thuringiensis israelensis* with molecular weights of 68 kDa, 125 kDa, and 135 kDa. However, the role of a fourth polypeptide of 28 kDa was still unclear. This invention presents a novel approach to elucidating the involvement of the 28 kDa protein in the toxicity of the crystals.

In vivo recombination in *B. thuringiensis israelensis* allowed the disruption of the cyta gene, encoding the 28 kDa polypeptide, on the 72 MDa resident plasmid. This was performed by a two-step mechanism, each of which involved a single crossover event. A very low frequency of recombination was first observed for the first event; this is unsurprising as the integration of the non-replicative plasmid is the result of both an event of transformation and recombination between two different plasmids. In contrast, the frequency of the second crossover was higher.

The high frequency of recombination found between fragments contained within the same plasmid is consistent with the observation of Gonzalez and Carlton (16), who found that the 72 MDa plasmid could be rearranged. These authors showed that the 72 MDa plasmid could recombine with a second resident plasmid (of 68 MDa), and then excised to give two plasmids of 80 MDa and 63 MDa; the resulting 63 MDa plasmid was found to be derived from the 72 MDa plasmid. It was also shown that i) several copies of the genes encoding the 125 kDa and 135 kDa polypeptides were present on this plasmid (6), and ii) both genes possess a nearly identical 3' region (6, 31, 39). It is therefore possible that deletions of the resident plasmid observed by Gonzalez and Carlton (16) could be the results of recombinations between these homologous regions.

The replacement of the native cyta gene by an interrupted copy was verified by Southern blot analysis. It was also shown that the strain in which only one crossover had occurred contained both the intact and disrupted cyta copy. The high intensity of the two hybridizing bands corresponding to the vector and the interrupted gene suggests that an amplification mechanism can also occur in *B. thuringiensis israelensis*. This event requires duplicated sequences and has already been described in another Gram (+) bacterium, *B. subtilis* (2, 23, 43). The fragments that are contained within the repeated sequences can be spontaneously amplified; the amplification level observed in *B. subtilis* ranges between 5 and 50 (23). Thus, a higher copy number of the fragments is found compared to that of the plasmid.

Protein analysis of the crystals produced by the recombinant strain from which the cyta gene has been disrupted showed that the corresponding product is absent in the crystals. The recombinant strain was found to produce the same amount of the 135 kDa, 125 kDa, and 68 kDa proteins as the parental strain. This suggests that elimination of one crystal component, at least the 28 kDa polypeptide, does not influence the expression of other crystal genes.

The strain containing the integrated recombinant plasmid produced an equal amount of 28 kDa protein as that found in the wild-type strain. This indicates that no titration of transcriptional regulatory factors occurs, when one intact and one truncated copy of the cyta gene are present.

Ibarra and Federici (21) previously showed that the parasporal body of *B. thuringiensis israelensis* consisted of three different inclusion types; they also suggested that each polypeptide composing the crystals could be associated within a specific inclusion type. These authors demonstrated that the 68 kDa protein was assembled separately in type 2 crystals, and they suggested that the 28 kDa polypeptide could be located in inclusion 1, the largest of the inclusions. On the other hand, Insell and Fitz-James (22) suggested that this protein could be assembled with the two high-molecular weight proteins, in the light density inclusion, probably corresponding to the type 1 inclusion.

It has now been discovered that the 28 kDa protein is not assembled separately from the other crystal components, as shown by electron microscopic studies of the strain in which this polypeptide is absent. Therefore, the 28 kDa protein could be associated with either inclusion types 1 or 3. Although the size and shape of the inclusions 1 and 3 produced by strains 4Q2-72 (cytA::erm) do not seem to be different from those originating from the wild-type strain 4Q2-72, we cannot exclude that the lattice structure of these inclusions could be different, even if preliminary calculation indicates the same lattice for inclusion type 1 in both cases.

It has been suggested that the 28 kDa protein is primarily responsible for the cytolytic activity of the solubilized crystals (reviewed in Federici et al. (13)). Surprisingly, it has now been found in mosquitocidal assays performed with the 28 kDa protein-free crystals that this polypeptide has only a minor effect on toxicity; moreover, this slight effect is restricted to *A. stephensi* larvae. The absence of 28 kDa protein from *B. thuringiensis israelensis* crystals had no effect on larvicidal activity for *A. aegypti* and *C. pipiens* larvae. Therefore, it seems that contrary to previous suggestions (10, 21, 42), the 28 kDa protein is not a key factor involved in a synergistic activity with other crystal components, at least on the three tested mosquito species.

Hemolytic assays performed with the 28 kDa protein-free crystals showed that this polypeptide is the only hemolytic component. The recombinant strain able to produce all but the 28 kDa polypeptides synthesized by the wild-type *B. thuringiensis israelensis* strain, could be useful in the control of vectors of tropical diseases. This strain, for which the activity is not significantly different from that of wild-type strain, does not produce the component found to be responsible for the lethality to mice after injection (33). Therefore, such constructed *B. thuringiensis israelensis* strain would be safer for field use than the wild-type one.

In vivo recombination in *B. thuringiensis israelensis* also provides a new tool to study the involvement of each toxin gene product in the mosquitocidal activity. Gene deletion in crystal producing strains combined with gene introduction into crystal minus strains can facilitate the determination of both the specific activity of each polypeptide and their participation in any synergy in the mode of action.

Recombination experiments could also be used to study the regulation of toxin genes. It has been shown that the expression of the cyta gene in *E. coli* was post-transcriptionally regulated by a polypeptide of 20 kDa. The gene for this protein has been located 4 kbp upstream from the cyta gene (1). This regulation has not yet been demonstrated in *B. thuringiensis israelensis*. With this novel approach, it is now possible to investigate the role of the 20 kDa polypeptide on the expression of the cytA gene as well as on other crystal protein genes.

*Bacillus thuringiensis* israelensis 4Q2-72 (cytA::erm) was deposited at the Collection Nationale de Cultures de Microorganismes, Institut Pasteur, 25 rue du Docteur Roux, 75724 Paris Cedex 15, on May 2, 1991, under Deposit No. I-1088.

The above disclosure generally describes the present invention. A more complete understanding can be obtained by reference to the following specific examples which are provided herein for purposes of illustration only and are not intended to be limiting unless otherwise specified.

EXAMPLES

Materials and Methods

Bacterial strains and plasmeds. *Escherichia coli* JM83 (ara Δlac-pro stra φ80Δalacz ΔM15) was used for the construction of recombinant plasmids. *Bacillus thuringiensis israelensis* 4Q2-72 (a gift from D. H. Dean, Ohio State University, Columbus) was used as a recipient strain for transformation experiments.

Plasmids. The recombinant plasmid pCB4, previously described (7) was the source of the cyta gene. The integrative vector, pJH101, was constructed by Ferrari et al. (14); it contains a cat gene conferring chloramphenicol resistance ($Cm^r$) when expressed in Gram (+) bacteria.

Figure 1:
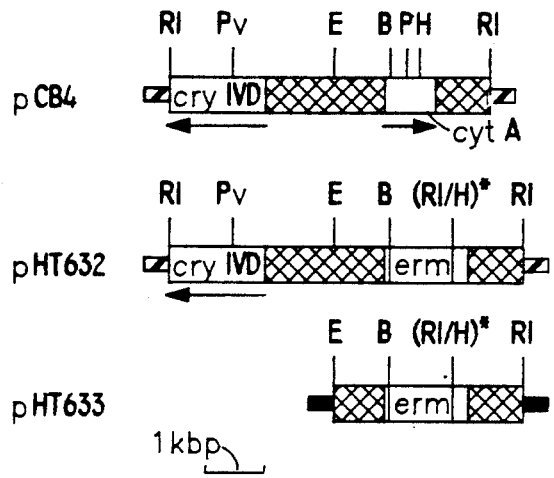
FIG. 1 shows restriction maps of recombinant plasmids. Plasmid pCB4, which has previously been described (7), contains both the cyta gene and part of the cryIVD gene. Plasmid pHT632 was constructed by replacing the 0.55 kbp BamHI-HpaI internal fragment of the cyta gene, by a 1.1.kbp EcoRI-HpaI erythromycin cassette. Plasmid pHT633 was obtained by subcloning the 3.1 kbp EcoRV-EcoRI from pHT632 into the vector pJH101. The arrows indicate the position and direction of transcription of the cryIVD and cyta genes. The symbol * indicates that both restriction sites have been lost. The vector pJH101 is represented by a black box.

Plasmid pHT632 was constructed as follows. A 1.1 kbp BamHI-EcoRI fragment containing both the promoter and the erm gene of the transposon Tn1545 was purified from plasmid pAT110 (34). This DNA fragment was cloned between the BamHI and HpaI restriction sites of plasmid pCB4, replacing a 0.55 kbp internal fragment of the cyta gene to yield the plasmid pHT632 (FIG. 1). The EcoRI was made blunt by using the Klenow fragment of DNA polymerase I.

Plasmid pHT633 was obtained by subcloning the 3.1 kbp EcoRV-EcoRI fragment, containing the interrupted gene, into the vector pJH101 cut with EcoRV-EcoRI (FIG. 1).

Transformation procedure. Transformation of *B. thuringiensis israelensis* was performed by electroporation essentially as described by Lereclus et al. (25), except that cells were grown in minimal medium supplemented with 0.5% (wt/vol) Casamino Acids (17) and harvested at an optical density at 650 nm of 0.5.

DNA manipulations. Protocols for restriction enzyme digestions, the use of DNA polymerase large fragment (Klenow fragment) and T4 DNA ligase were carried out as described by Maniatis et al. (26). All enzymes were used as recommended by the manufacturers.

Recombinant plasmids were isolated from *E. coli* by the alkaline denaturation method of Birnboim and Doly (5). Plasmids were subsequently purified by centrifugation on a cesium chloride gradient.

Total DNA was isolated from *B. thuringiensis* cells grown in Luria medium (28), which were harvested during the exponential phase ($A_{650}$ about 1.5). Cells were suspended in 1/10 volume of 0.1M Tris-HCl (pH 8), 0.1M EDTAT 0.15M NaCl and incubated in the presence of lysozyme (1 mg/ml) for 30 min. at 37° C. The samples were treated with pancreatic RNAse (100 mg/ml for 30 min., at 50° C.), and sodium dodecyl sulfate was then added to 1% (wt/vol) and the preparation was further incubated for 20 min. at 70° C. Proteinase K (500 mg/ml) was then added, and incubation continued for 2 h at 45° C. Phenol extractions were then carried out followed by isopropanol precipitation. The DNA was drawn out of solution by being wound around a glass rod, and then suspended in 10 mM Tris-HCl (pH 8), 1 Mm EDTA.

DNA was analyzed by electrophoresis on 0.6% horizontal agarose slab gels. Hybridization experiments were performed on nitrocellulose filters as described by Southern (32). The DNA was labeled with a nick-translation kit (Boehringer Mannheim) and [$\alpha$-$^{32}$P] dCTP (110 TBq/mmol), as described by the manufacturer.

Protein analysis. *B. thuringiensis* cells were grown in HCT medium (24), supplemented with antibiotics if necessary, with shaking at 30° C. up to cell lysis. Spores and crystals were harvested, washed once in 1M NaCl and twice in 1 Mm phenylmethysulphonyl fluoride, 10 mM EDTA. Samples were then subjected to electrophoresis on 10% sodium dodecyl sulfate polyacrylamide gels or further purified on discontinuous sucrose gradient as described by Thomas and Ellar (33), except that sucrose was dissolved in 50 Mm Tris-HCl (pH 7.5).

Crystals were solubilized by incubation at 37° C. for 30 min. in the presence of 0.05N NAOH. Insoluble material was removed by centrifugation at 10,000 rpm for 5 min.

Protein concentrations were measured by the Bio-Rad Assay after alkali-solubilization of the crystals.

Sodium dodecyl sulfate-polyacrylamide gel electrophoresis and immunoblotting using rabbit antiserum raised against *B. thuringiensis israelensis* crystals were performed as described by Delecluse et al. (12).

Electron microscopy. Cells were grown at 30° C. with shaking in HCT medium supplemented with erythromycin (8 μg/ml) when necessary, and harvested after 40 h culture. Samples (2 ml) were thawed and treated as described by Charles et al. (8), except that 0.1M cacodylate buffer was used instead of sodium phosphate buffer.

Assay for hemolytic activity. Sheep red blood cells were washed twice in 0.015M Tris-HCl (pH 8), 0.17M NaCl and diluted in 100 volumes of the same buffer. A sample of this solution (1 ml) was added to the material to be assayed and incubated at 37° C. for 30 min. The samples were then centrifuged at 5000 rpm for 2 min. and the amount of hemoglobin released was estimated by measuring the absorbance of the supernatant at 540 nm. In these conditions, an optical density at 540 nm of 1 is equivalent to 100% lysis (3).

Mosquitocidal activity assay. Purified crystals were diluted in glass Petri dishes containing 10 ml of deionized water and 0.5 mg. of yeast extract and tested against larvae of *Aedes aegypti* (fourth instar), *Anopheles stephensi* (third instar), or *Culex pipens* (fourth instar). Mortality was scored after 24 h incubation at 27° C. Each sample was independently assayed four times in duplicate, and the $LC_{50}$ s (concentration of crystal protein giving 50% mortality) were determined by Probit analysis.

EXAMPLE 1

Disruption of the cytA Gene Present on the 72 MDa Resident Plasmid

Gene disruption analysis was carried out to study the involvement of the 28 kDa polypeptide in the toxicity of the *B. thuringiensis israelensis* crystals. The cyta gene was disrupted by replacing an internal fragment of the cyta gene with an erythromycin resistance determinant as described in Materials and Methods.

The recombinant plasmid pHT633 (FIG. 1) purified from *E. coli*, was introduced into the toxic *B. thuringiensis israelensis* strain 4Q2-72 by electroporation as described in Materials and Methods. Transformants resistant to erythromycin ($Em^r$) were selected. Since the plasmid pHT633 does not contain a Gram (+) replicon, resistance can only result from integration of the erm gene into the 72 MDa plasmid. Integration via single or double crossover can occur by homologous recombination between the resident plasmid and the *B. thuringiensis israelensis* DNA fragments flanking the erm gene, which are approximately 1 kbp in length (FIG. 1). As shown in FIG. 2A, an event involving only one crossover (Campbell mechanism) leads to the integration of the entire plasmid, and therefore confers resistance to chloramphenicol (Cm). The $Em^r$ transformants obtained were $Cm^r$ suggesting that pHT633 had integrated into the 72 MDa plasmid by a Campbell mechanism. The frequency of integration was $10^2$ $Em^r$ transformants per mg of transforming plasmid DNA. The transformation conducted in parallel with the plasmid pHT3101 able to replicate in *B. thuringiensis israelensis* and conferring $Em^r$ (25) gave $5 \times 10^6$ transformants per mg of DNA. Therefore, single intermolecular recombination with the resident plasmid occurs in *B. thuringiensis israelensis* at a rate of approximately $2 \times 10^{-5}$. The integrants contained both the wild-type cytA gene and the disrupted cytA gene separated by the vector pJH101 (FIG. 2A). The integration therefore created a duplication of the regions flanking the erm gene, between which a second element of recombination could occur (FIG. 2B). This event would eliminate the regions contained within the two homologous parts including the vector and the intact cytA gene.

To obtain such a deletion by recombination, 4Q2-72 (::pHT633) cells were grown in Luria medium containing erythromycin, to avoid the loss of the interrupted gene, but in the absence of chloramphenicol at 37° C. for 6 hours. Dilutions of culture were then plated on erythromycin medium and colonies screened for sensitivity to chloramphenicol. About one in three $Em^r$ colonies were $Cm^s$, and had therefore lost the Cm marker. This experiment indicates that in vivo recombinations can occur in *B. thuringiensis israelensis*, thus enabling gene replacements. One $Em^r$ $Cm^s$ clone 4Q2-72 (cytA::e.rm), in which the cytA gene has been insertionally activated, was chosen and used for further experiments.

EXAMPLE 2

Analysis of the Modified 72 MDa Resident Plasmid

Replacement of the cytA gene on the 72 MDa plasmid by an interrupted copy was confirmed by Southern blot analysis of total DNA. Total DNA from strains 4Q2-72, 4Q2-72 (::pHT633), and 4Q2-72 (cytA::erm), prepared as described in Materials and Methods, were digested either with EcoRI or with EcoRI and EcoRV. As a control, plasmid pHT633 was digested with EcoRI and EcoRV. The fragments were separated by agarose gel electrophoresis, transferred onto nitrocellulose membranes, and hybridized with labeled pHT633 as a probe. The resulting hybridization pattern is shown in FIG. 3. In the 4Q2-72 (cytA::erm) sample, only one EcoRIEcoRV fragment of 3.1 kbp hybridized with the probe (FIG. 3A, lane 3), indicating that only one copy is present in this strain. The hybridizing fragment has the same size as the lowest hybridizing band of the control pHT633, which corresponds to the interrupted gene (FIG. 3A, lane P). A fragment of 2.8 kbp corresponding to the intact gene was found in the strain 4Q2-72 (FIG. 3A, lane 1). Three hybridizing bands of 5.4 kbp, 3.1 kbp and 2.8 kbp are observed in the strain 4Q2-72 (::pHT633), which contains one intact copy of the cytA gene and one interrupted copy (FIG. 3A, lane 2). These fragments correspond to the vector, the cytA::erm, and the cytA gene, respectively. The high intensity of the 5.4 kbp and 3.1 kbp fragments will be discussed below.

The hybridization analysis of EcoRI digested DNA allowed the site of the first crossover event to be determined (FIG. 3B). Since the erm gene is flanked by two parts of the cytA gene, the first crossover could have occurred either upstream or downstream from the erm gene (FIG. 2A(a) and (b), respectively). DNA from strain 4Q2-72 (::pHT633) digested with EcoRI contained two bands of 8.5 kbp and 5.6 kbp (FIG. 3B, lane 2); the smaller band co-migrates with that found in the strain 4Q2-72 (FIG. 3B, lane 1), indicating that the first crossover occurred in the downstream region of the erm gene (FIG. 2Ab); the larger EcoRI fragment corresponds to both the interrupted cytA gene copy and the pJH101 vector. The intensity observed for that band will be discussed below. The hybridizing fragment of 6 kbp found in the strain 4Q2-72 (cytA::erm) (FIG. 3B, lane 3) includes the cytA::erm and the upstream region containing part of the cryIVD gene.

Therefore, it has been demonstrated that in the recombinant strain 4Q2-72 (cytA::erm), the intact copy of the cytA gene was replaced with an interrupted copy corresponding to a cytA::erm transcriptional fusion.

EXAMPLE 3

Composition and Structure of Crystal

The composition of the crystals synthesized by the strains either deleted of the 28 kDa protein gene or containing both the intact and interrupted cytA genes was analyzed and compared to that produced by the wild-type strain.

Cells from strains 4Q2-72, 4Q2-72 (::pHT633), and 4Q2-72 (cytA::erm) were grown with shaking in HCT medium at 30° C. for 60 h up to cell lysis; erythromycin and chloramphenicol (8 μg/ml and 5 μg/ml, respectively) or erythromycin (8 μg/ml) were added to the medium for the strains 4Q2-72 (::pHT633) and 4Q2-72 (cytA::erm), respectively. Cells were harvested at the end of sporulation and treated as described in Materials and Methods. Samples which consisted of spore and crystal mixtures were subjected to sodium dodecyl sulfate-polyacrylamide gel electrophoresis and the gel was then stained with Coomassie brilliant blue (FIG. 4A).

No major difference was observed between the polypeptides synthesized by the 4Q2-72 (::pHT633) (FIG. 4A, lane 2) and the wild-type strain (FIG. 4A, lane 1). Both produced the 28 kDa protein as well as the other polypeptides of crystal (68, 125 and 135 kDa) in equal amounts. In contrast, as expected, 4Q2-72 (cytA::erm) did not synthesize the 28 kDa protein (FIG. 4A, lane 3). However, a faint band of about 28 kDa was present in this strain. This polypeptide could be a degradation product of a higher molecular weight protein. Immunodetection after sodium dodecyl sulfate-polyacrylamide gel electrophoresis of the polypeptides produced by the 4Q2-72 (cytA::erm) confirmed this hypothesis, since no band of about 28 kDa reacted with the antibodies specific for B. thuringiensis crystal protein (FIG. 4B, lane 3). The immunoreaction patterns of the wild-type and the 4Q2-72 (::pHT633) strains were indistinguishable (FIG. 4B, lanes 1 and 2, respectively).

Ultrathin sections of strains 4Q2-72 and 4Q2-72 (cytA::e.rm) were examined under an electron microscope to assess differences in crystal size and shape due to the absence of one crystal component. Cells were grown at 30° C. with shaking in HCT medium supplemented with erythromycin (8 μg/ml) for the 4Q2-72 (cytA::erm) and harvested after 40 h culture. Samples were treated as described in Materials and Methods and observed under transmission electron microscope. No major difference of crystal structure was found when comparing the parasporal bodies produced by strain 4Q2-72 (FIG. 5A) and 4Q2-72 (cytA::erm) (FIG. 5B). For both strains the parasporal body is basically spherical in shape and delimited by an envelope. The structure of the crystals, which are composite in the strain 4Q2-72 (FIG. 5A), appears to be similar to those in strain 4Q2-72 (cytA::erm) (FIG. 5B). In each case, three types of inclusions are found, designated type 1, 2, and 3, according to Ibarra and Federici (21).

EXAMPLE 4

Involvement of the 28 kDa Protein in Hemolytic Activity and Mosquitocidal Toxicity Crystalline inclusions from both strains were separated from spores and purified by ultracentrifugation on discontinuous sucrose density gradients as described in Materials and Methods. Purified crystals from strains 4Q2-72 and 4Q2-72 (cytA::erm) were assayed for mosquitocidal and hemolytic activity.

The hemolytic activity of the inclusions was tested on sheep red blood cells (see Materials and Methods). Prior to the assay, crystals were solubilized by incubation with 0.05 N NAOH, since it has been shown that native crystals were not hemolytic (33). The soluble crystal proteins from strain 4Q2-72 were found to be hemolytic, with a concentration of about 2.7 μg/ml giving 50% hemolysis. In contrast, 100 μg/ml of the crystals depleted of the 28 kDa protein caused hemolysis equivalent to the background level of the buffer control.

The activity of crystals produced by either the wild-type strain or 4Q2-72 (cytA::erm) was tested on larvae of Aedes aegypti, Anopheles stephensi, and Culex pipiens (see Materials and Methods). Toxicity to A. aegypti larvae of the crystals depleted of the 28 kDa did not differ significantly from that of the crystals containing all the polypeptides; $LC_{50}$ were 13 and 11.9 ng/ml for 4Q2-72 (cytA::e.rm) and 4Q-72, respectively. In the same way, toxicity to C. pipiens larvae of the crystals in which the 28 kDa protein has been removed was equivalent to that of the native crystals. In contrast, on A. stephensi larvae, the absence of the 28 kDa protein had a slight effect the activity of 4Q2-72 (cytA::erm) ($LC_{50}$:7.7 ng/ml) was half that of the wild-type strain 4Q2-72 ($LC_{50}$:4.9 ng/ml).

These results indicate that the 28 kDa polypeptide contributes slightly to the toxicity to A. stephensi larvae, but is inactive in the mosquitocidal activity towards A. aegypti and C. pipiens larvae.

EXAMPLE 5

A derivative of strain 4Q2-72 (cytA::erm) was constructed. This strain contains an interrupted cytA gene, but the erm gene has been eliminated.

The construction was performed as follows. In a first step, plasmid pHT635 (see FIG. 6) was introduced into strain 4Q2-72 (cytA::erm) by electroporation as described above. Recombinants which had integrated the plasmid pHT635 into the 72 MDa resident plasmid were selected on chloramphenicol (5 μg/ml). The integrants contained both a cytA::erm gene and the newly introduced disrupted cytA gene, separated by the vector pJH101. The integration created again a duplication of the regions flanking the erm gene, between which a second event of recombination could occur. To obtain such an event, integrants were grown in the absence of both chloramphenicol and erythromycin as previously described for construction of strain 4Q2-72 (cytA::erm). Dilutions of culture were then plated on non-selective medium, and the colonies were screened for their sensitivity to both antibiotics. Colonies which had lost the erm and cm markers were chosen; these clones contain a disrupted cytA gene but have lost all foreign DNA originating from E. coli including the antibiotic resistance markers.

One clone 4Q2-72 (ΔcytA) was chosen for further experiments. It is non hemolytic but still active against mosquito larvae. Since it contains no foreign DNA and has been obtained by in vivo recombination, this clone seems convenient to be used in biological control against mosquito larvae.

Having now generally described the invention, it will be readily apparent to those skilled in the art that many changes and modifications can be made thereto without affecting the spirit and scope thereof.

LITERATURE CITED

1. Adams, L. F., J. E. Visick, and H. R. Whiteley. 1989. A 20-kilodalton protein is required for efficient production of the *Bacillus thuringiensis* subsp. *israelensis* 27-kilodalton crystal protein in *Escherichia coli*. J. Bacteriol. 171:521–530.

2. Albertini, A. M., and A. Galizzi. 1985. Amplification of a chromosomal region in *Bacillus subtilis*. J. Bacteriol. 162:1203–1211.

3. Aloof, J. E., M. Viette, R. Corvazier, and M. Raynaud. 1965. Preparation et proprietes de serums de chevaux anti-streptolysine 0. Ann. Inst. Pasteur 108:476–500.

4. Armstrong, J. L., G. F. Rohrman, and G. S. Beaudreau. 1985. Delta endotoxin of *Bacillus thuringiensis* subsp. *israelensis*. J. Bacteriol. 161:39–46.

5. Birnboim, H. C., and J. Doly. 1979. A rapid alkaline extraction procedure for screening recombinant plasmid DNA. Nucleic Acids Res. 7:1513–1523.

6. Bourgouin, C., A. Delecluse, J. Ribier, A. Klier, and G. Rapoport. 1988. A *Bacillus thuringiensis* subsp. *israelensis* gene encoding a 125-kilodalton larvicidal polypeptide is associated with inverted repeat sequences. J. Bacteriol. 170:3575–3583.

7. Bourgouin, C., A. Klier, and G. Rapoport. 1986. Characterization of the genes encoding the haemolytic toxin and the mosquitocidal delta-endotoxin of *Bacillus thuringiensis israelensis*. Mol. Gen. Genet. 205:390–397.

8. Charles, J. P., L. Nicolas, M. Sebald, and H. de Barjac. 1990. *Clostridium bifermentans* serovar *malaysia*: sporulation, biogenesis of inclusion bodies and larvicidal effect on mosquito. Res. Microbiol. 141:721–733.

9. Cheung,, P. Y. K., and B. D. Hamock. 1985. Separation of three biologically distinct activities from the parasporal crystal of *Bacillus thuringiensis* var. *israelensis*. Curr. Microbiol. 12:121–126.

10. Chilcott, C. N., and D. J. Ellar. 1985. Comparative toxicity of *Bacillus thuringiensis* var. *israelensis* crystal proteins in vivo and in vitro. J. Gen. Microbiol. 134:2551–2558.

11. Davidson,, E. W., and T. Yamamoto. 1984. Isolation and assay of the toxic component from the crystals of *Bacillus thuringiensis* var. *israelensis*. Curr. Microbiol. 11:171–174.

12. Delecluse, A., C. Bourgouin, A. Klier, and G. Rapoport. 1988. Specificity of action on mosquito larvae of *Bacillus thuringiensis* israelensis toxins encoded by two different genes. Mol. Gen. Genet..214:42–47.

13. Federici, B. A.; P. Luthy, and J. E. Ibarra. 1990. Parasporal body of *Bacillus thuringiensis israelensis*. Structure, protein composition, and toxicity, p. 16–44. In H. de Barjac, and D. J. Sutherland (ed.), Bacterial Control of Mosquitoes and Black Flies; Biochemistry, Genetics and Applications of *Bacillus thuringiensis israelensis* and *Bacillus sphaericus*. Rutgers University Press, New Brunswick.

14. Ferrari, F. A., A. Nguyen, D. Lang, and J. A. Hoch. 1983. Construction and properties of an integrable plasmid for *Bacillus subtilis*. J. Bacteriol. 154:1513–1515.

15. Goldberg, L. H., and J. Margalit. 1977. A bacterial spore demonstrating rapid larvicidal activity against *Anopheles sergentii, Uranotaenia unguiculata, Culex univitatus, Aedes aegypti* and *Culex pipiens*. Mosq. News 37:355–358.

16. Gonzalez, J. M. Jr., and B. C. Carlton. 1984. A large transmissible plasmid is required for crystal toxin production in *Bacillus thuringiensis* variety *israelensis*. Plasmid 11:28–38.

17. Heierson, A., R. Landen, A. Lovgren, G. Dalhammar, and E. G. Boman. 1987. Transformation of vegetative cells of *Bacillus thuringiensis* by plasmid DNA. J. Bacteriol. 169:1147–1152.

18. Heldy G. A., Y. S. Huang, and C. Y. Kawanishi. 1986. Effect of removal of the cytolytic factor of *Bacillus thuringiensis* subsp. *israelensis* on mosquito toxicity. Biochem. Biophys. Res. Commun. 141:937–941.

19. Hofte, H., and H. R. Whiteley. 1989. Insecticidal crystal proteins of *Bacillus thuringiensis*. Microbiol. Rev. 53:242–255.

20. Hurley, J. M., S. G. Lee, R. E. Andrews Jr., M. J. Klowden, and L. A. Bulla Jr. 1985. Separation of the cytolytic and mosquitocidal proteins of *Bacillus thuringiensis* subsp. *israelensis*. Biochem. Biophys. Res. Commun. 126:961–965.

21. Ibarra, J. E., and B. A. Pederici. 1986. Isolation of a relatively nontoxic 65-kilodalton protein inclusion from the parasporal body of *Bacillus thuringiensis* subsp. *israelensis*. J. Bacteriol. 165:527–533.

22. Insell, J. P., and P. C. Fitz-James. 1985. Composition and toxicity of the inclusion of *Bacillus thuringiensis* subsp. *israelensis* Appl. Environ. Microbiol. 50:56–62.

23. Janniere, L., B. Niaudet, E. Pierre, and S. D. Ehrlich. 1985. Stable gene amplification in the chromosome of *Bacillus subtilis*. Gene 40:47–55.

24. Lecadet, M-M., M-0. Blondel, and J. Ribier. 1980. Generalized transduction in *Bacillus thuringiensis* var. Berliner 1715, using bacteriophage CP$_{54}$ Ber.J. Gen. Microbiol. 121:202–212.

25. Lereclus, D., O. Arantes, J, Chaufaux,, and M-M. Lecadet. 1989. Transformation and expression of a cloned δ-endotoxin gene in *Bacillus thuringiensis*. FEMS Microbiol. Lett. 60:211–218.

26. Maniatis, T., E. F. Fritech, and J. Sambrook. 1982. Molecular cloning: a laboratory manual. Cold Spring Harbor Laboratory, Cold Spring Harbor, N.Y.

27. McLean, K. M., and H. R. Whiteley. 1987. Expression in *Escherichia coli* of a cloned crystal protein gene of *Bacillus thuringiensis* subsp. israelensis. J. Bacteriol. 169:1017–1023.

28. Miller, J. H. 1972. Experiments in Molecular Genetics. Cold Spring Harbor Laboratory, Cold Spring Harbor, N.Y.

29. Nishiura, J. T. 1988. Fractionation of two mosquitocidal activities from alkali-solubilized extracts of *Bacillus thuringiensis* subspecies israelensis spores and parasporal inclusions. J. Invertebr. Pathol. 51:15–22.

30. Pfannenstiel, M. A., G. A. Coucher, E. J. Ross, and K. W. Nickerson. 1986. Immunological relationships among proteins making up the *Bacillus thuringiensis* subsp. *israelensis* crystalline toxin. Appl. Environ. Microbiol. 52:644–649.

31. Sen, K., G. Honda, N. Koyama, M. Nishida, A. Neki, H. Sakai, M. Himeno, and T. Komano. 1988. Cloning and nucleotide sequences of the two 130 kDa insecticidal protein genes of *Bacillus thuringiensis* var. *israelensis*. Agric. Biol. Chem. 52:873–878.

32. Southern, E. M. 1975. Detection of specific sequences among DNA fragments separated by gel electrophoresis. J. Mol. Biol. 98:503–517.

33. Thomas, W. E., and D. J. Ellar. 1983. *Bacillus thuringiensis* var. *israelensis* crystal δ-endotoxin: effects on insect and mammalian cells in vitro and in vivo. J. Cell Sci. 60:181–197.

34. Trieu-Cuot, P., C. Poyart-Salmeron, C. Carlier, and P. Courvalin. 1990. Nucleotide sequence of the erythromycin resistance gene of the conjugative transposon Tn1545. Nucleic Acids Res. 18:3660.

35. Undeen, A., and W. Nagel. 1978. The effect of *Bacillus thuringiensis* ONR60A strain (Goldberg) on Simulium larvae in the laboratory. Mosq. News 38:524–257.

36. Visser, B., M. van Workum, A. Dullemans; and C. Waalwijk 1986. The mosquitocidal activity of *Bacillus thuringiensis* var. *israelensis* is associated with Mr 230,000 and 130,000 crystal proteins. FEMS Microbiol. Lett. 30:211–214.

37. Ward, E. S., and D. J. Ellar. 1983. Assignment of the δ-endotoxin gene of *Bacillus thuringiensis* var. *israelensis* to a specific plasmid by curing analysis. FEBS Lett. 158:45–49.

38. Ward,, E. S., and D. J. Ellar. 1986. *Bacillus thuringiensis* var. *israelensis* δ-endotoxin. Nucleotide sequence and characterization of the transcripts in *Bacillus thuringiensis* and *Escherichia coli*. J. Mol. Biol. 191:1–11.

39. Ward, E. S., and D. J. Ellar. 1988. Cloning and expression of two homologous genes of *Bacillus thuringiensis* subsp. laraelansis which encode 130-kilodalton mosquitocidal proteins. J. Bacteriol. 170:727–735.

40. Ward,, E. S., D. J. Ellar, and J. A. Todd. 1984. Cloning and expression in *Escherichia coli* of the insecticidal δ-endotoxin gene of *Bacillus thuringiensis* var. *israelensis*. FEBS Lett. 175:377–382.

41. Ward, E. S., A. R. Ridleyl D. J. Ellar, and J. A. Todd. 1986. *Bacillus thuringiensis* var. *israelensis* δ-endotoxin. Cloning and expression of the toxin in sporogenic and asporogenic strains of *Bacillus subtilis*. J. Mol. Biol. 191:13–22.

42. Wu, D., and F. N. Chang. 1985. Synergism in mosquitocidal activity of 26 and 65 kDa proteins from *Bacillus thuringiensis* subsp. *israelensis* crystal. FEBS Lett. 190:232–236.

43. Young, M. 1984. Gene amplification in *Bacillus subtilis*. J. Gen. Microbiol. 130:1613–1621.

What is claimed:

1. An isolated and purified recombinant molecule comprising a nucleic acid that encodes on expression all of the polypeptides displaying mosquito larvicidal activity expressed in a wild type *Bacillus thuringiensis* subtype and wherein all DNA sequences encoding polypeptides displaying hemolytic activity have been disrupted or eliminated.

2. The recombinant molecule of claim 1, wherein said polypeptides displaying mosquito larvicidal activity comprise the 68 kDa, 125 kDa and 135 kDa polypeptide components of *Bacillus thuringiensis israelensis* crystalline inclusions.

3. The recombinant molecule of claim 1, wherein said nucleic acid is operatively linked to an expression control sequence.

4. A *Bacillus thuringiensis* microorganism transformed with the nucleic acid of claim 3, wherein said polypeptides are is capable of being expressed in said microorganism.

5. The microorganism of claim 4, wherein said microorganism is *Bacillus thuringiensis israelensis*.

6. The microorganism *Bacillus thuringiensis israelensis* 4Q2-72 (cytA::erm).

7. A biologically pure culture of the microorganism *Bacillus thuringiensis israelensis* 4Q2-72 (Δcyt A).

* * * * *

UNITED STATES PATENT AND TRADEMARK OFFICE
CERTIFICATE OF CORRECTION

PATENT NO. : 5,304,484
DATED : April 19, 1994
INVENTOR(S) : Armelle DELECLUSE et al.

It is certified that error appears in the above-indentified patent and that said Letters Patent is hereby corrected as shown below:

Claim 4, col. 14, line 30, delete the word "is".

Abstract, line 1, "cyta" should read -- cytA--.

Signed and Sealed this

Second Day of August, 1994

Attest:

BRUCE LEHMAN

Attesting Officer    Commissioner of Patents and Trademarks